United States Patent [19]

Franckowiak et al.

[11] Patent Number: 4,876,255
[45] Date of Patent: Oct. 24, 1989

[54] SUBSTITUTED 1,4-DIHYDROPYRIDINES FOR CONTROL OF CIRCULATION AND THROMBOSES

[75] Inventors: Gerhard Franckowiak; Ulrich Rosentreter; Elisabeth Perzborn; Friedel Seuter, all of Wuppertal; Michael Kayser, Leverkusen, all of Fed. Rep. of Germany; Günther Thomas, Arese, Italy

[73] Assignee: Bayer Aktiengesellschaft, Leverkusen, Fed. Rep. of Germany

[21] Appl. No.: 178,710

[22] Filed: Apr. 7, 1988

[30] Foreign Application Priority Data

Apr. 11, 1987 [DE] Fed. Rep. of Germany ....... 3712371

[51] Int. Cl.[4] .................... C07D 401/12; A61K 31/50
[52] U.S. Cl. ..................................... 514/252; 544/238; 544/239
[58] Field of Search ................. 544/238, 239; 514/252

[56] References Cited

U.S. PATENT DOCUMENTS 4,705,794 11/1987 Wehinger et al. ................. 544/238
4,707,479 11/1987 Meyer et al. ....................... 544/238
4,777,256 10/1988 Ueda et al. ........................ 544/238

FOREIGN PATENT DOCUMENTS 3431862 3/1986 Fed. Rep. of Germany .
3445852 6/1986 Fed. Rep. of Germany .

Primary Examiner—Nicholas S. Rizzo
Attorney, Agent, or Firm—Sprung Horn Kramer & Woods

[57] ABSTRACT

For the control of coronary diseases and thromboses there are provided the novel compounds

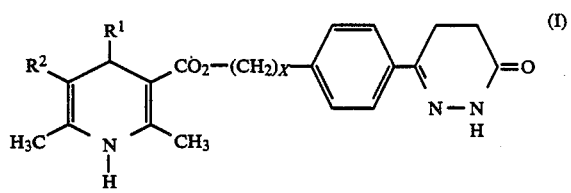

in which
  $R^1$ is an optionally substituted phenyl or heterocyclic radical,
  $R^2$ is a cyano, keto, carboxy, ester or amide group, and
  X is from 0 to 6,
and physiologically acceptable salts thereof.

12 Claims, No Drawings

SUBSTITUTED 1,4-DIHYDROPYRIDINES FOR CONTROL OF CIRCULATION AND THROMBOSES

The invention relates to substituted 1,4-dihydropyridines, several processes for their preparation and their use in medicaments, in particular for the control of circulatory diseases and thromboses.

The present invention relates to substituted 1,4-dihydropyridines of the general formula (I)

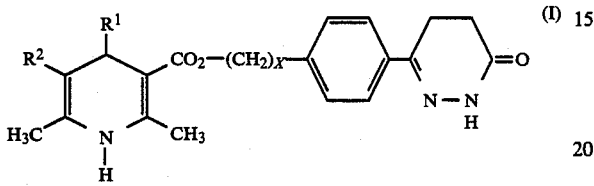

in which $R^1$ represents $C_6$–$C_{14}$-aryl, which may be mono-, di-, tri- or tetrasubstituted (the substituents being identical or different) by halogen, nitro, cyano, $C_1$–$C_6$-alkyl, $C_1$–$C_6$-alkoxy, $C_1$–$C_6$-alkylthio, trifluoromethyl, trifluoromethoxy, difluoromethoxy trifluoromethylthio or by benzyloxy, benzylthio or, benzyl which is optionally substituted by nitro, cyano, trifluoromethyl, $C_1$–$C_4$-alkyl or $C_1$–$C_4$-alkoxy or represents an optionally halogen-, phenyl- or $C_1$–$C_4$alkyl-substituted heterocycle from the series pyrryl, thienyl, furyl, pyrazolyl, imidazolyl, oxazolyl, thiazolyl, pyridyl, pyridazinyl, pyrimidyl, quinolyl, benzoxadiazolyl, chromenyl or thiochromenyl, or represents straight-chain, branched or cyclic alkyl with up to 6 carbon atoms, which is optionally substituted by pyridyl, pyrimidyl, halogen or nitro, $R^2$ represents cyano or a group of the formula

wherein $R^3$ denotes straight-chain, branched or cyclic alkyl with up to 8 carbon atoms, or denotes a group of the formula

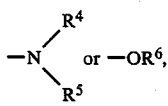

wherein $R^4$ and $R^5$ are identical or different and represent hydrogen, $C_1$–$C_6$-alkyl, phenyl or benzyl, and $R^6$ represents hydrogen or represents straight-chain, branched or cyclic alkyl, which can be substituted by halogen, cyano, hydroxyl, $C_1$–$C_8$-alkoxy, pyridyl, pyrimidyl, thienyl, furyl or by phenyl which is optionally substituted by halogen, nitro, cyano, trifluoromethyl, $C_1$–$C_4$-alkyl, $C_1$–$C_4$-alkoxy or a group of the formula

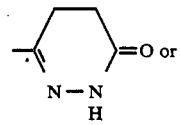

by phenoxy, phenylthio, phenylsulphonyl or by a group of the formula

wherein $R^7$ and $R^8$ are identical or different and represent hydrogen, $C_1$–$C_6$-alkyl, phenyl, benzoyl, phenethyl, acetyl, benzoyl, phenylsulphonyl or $C_1$–$C_4$-alkylsulphonyl, or $R^7$ and $R^8$, together with the nitrogen atom, form a 5- to 7-membered ring, which can optionally contain oxygen, sulphur, NH, N-phenyl or N-$C_1$–$C_4$alkyl or N-benzyl as a further hetero moiety, and X represents a number from 0 to 6, and their physiologically acceptable salts.

Those compounds of the general formula (I) are preferred in which $R^1$ represents phenyl or naphthyl, which may be mono-, di- or trisubstituted (the substituents being identical or different) by fluorine, chlorine bromine, nitro, cyano, $C_1$–$C_4$-alkyl, $C_1$–$C_4$-alkoxy, $C_1$–$C_4$-alkylthio, trifluoromethyl, difluoromethoxy, trifluoromethoxy, trifluoromethylthio, benzylthio or benzyloxy which is optionally substituted by nitro, fluorine, chlorine, bromine, trifluoromethyl, methyl or methoxy, or represents an optionally methyl-, fluorine-, chlorine-, bromineor phenyl-substituted heterocycle from the series thienyl, furyl, pyridyl, pyrimidyl, quinolyl, benzoxadiazolyl or thiochromenyl, or represents straight-chain or branched, optionally fluorine-, chlorine-, bromine- or pyridyl- substituted alkyl with up to 4 carbon atoms, $R^2$ represents cyano or a group of the formula

wherein $R^3$ represents straight-chain, branched or cyclic alkyl with up to 6 carbon atoms, or represents a group of the formula

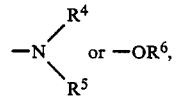

where $R^4$ and $R^5$ are identical or different and represent hydrogen, $C_1$–$C_4$-alkyl or phenyl, and $R^6$ represents hydrogen or represents stright-chain or branched alkyl with up to 8 carbon atoms, which can be substituted by up to 7 fluorine atoms, or by chlorine, bromine, cyano, hydroxyl, $C_1$–$C_6$-alkoxy, pyridyl, phenoxy or by phenyl which is optionally substituted by fluorine, chlorine, bromine, nitro, cyano, trifluoromethyl, $C_1$–$C_2$-alkyl, $C_1$–$C_2$-alkoxy or a group of the formula

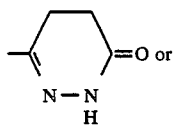

by a group of the formula

where $R^7$ and $R^8$ are identical or different and represent hydrogen, $C_1$–$C_4$-alkyl, phenyl, benzyl or acetyl, or $R^7$ and $R^8$ together form a 5- to 7-membered ring, which optionally contains sulphur or oxygen as a further hetero atom, and X represents a number from 0 to 5, and their physiologically acceptable salts.

Those compounds of the general formula (I) are particularly preferred in which $R^1$ represents phenyl, which may be mono- or disubstituted (the substituents being identical or different) by fluorine, chlorine, nitro, cyano, $C_1$–$C_4$-alkyl, $C_1$–$C_4$-alkoxy, trifluoromethyl, benzyloxy or benzylthio, or represents thienyl, furyl, pyridyl or benzoxadiazolyl, or represents a heterocycle of the formula

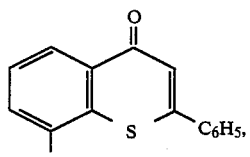

or represents an optionally $\alpha$-, $\beta$- or $\gamma$-pyridylsubstituted methyl or ethyl, and $R^2$ represents cyano or a group of the formula

wherein $R^3$ represents straight-chain or branched alkyl with up to 4 carbon atoms, or represents a radical of the formula

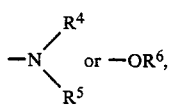

where $R^4$ and $R^5$ are identical or different and represent hydrogen, methyl or ethyl and $R^6$ represents hydrogen or represents a straight-chain or branched alkyl with up to 6 carbon atoms, which may be mono-, di- or trisubstituted by fluorine, chlorine, bromine, cyano, hydroxyl, $C_{1-4}$-alkoxy, $\alpha$-, $\beta$- or $\gamma$-pyridyl or by a gorup of the formula

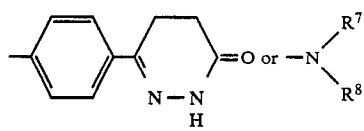

wherein $R^7$ and $R^8$ are identical or different and represent hydrogen, methyl, ethyl or benzyl, or $R^7$ and $R^8$ together form a pyrrolidino or piperidino ring, and X represents a number from 1 to 4, and their physiologically acceptable salts.

Physiologically acceptable salts are salts of the compounds according to the invention with inorganic or organic acids. Preferably included here are inorganic acids such as hydrohalic acids, preferably HCl or HBr, sulphuric acid, phosphoric acid, or organic carboxylic acids or sulphonic acids such as, for example, acetic acid, maleic acid, fumaric acid, malic acid, citric acid, tartaric acid, lactic acid, benzoic acid, methanesulphonic acid, ethanesulphonic acid, benzenesulphonic acid, naphthalenedisulphonic acid or toluenesulphonic acid.

The compounds according to the invention exist in stereosiomeric forms, which behave either as image and mirror images (enantiomers) or do not behave as image and mirror images (diastereomers). The invention relates both to the antipodes and to the racemic forms and also to the diastereomeric mixtures. The racemic forms, like the diastereomers, can be separated into the individual stereoisomeric constituents in known ways [cf. E.L. Eliel, Stereochemistry of Carbon Compounds, McGraw Hill, 1962].

The compounds according to the invention of the general formula (I) are obtained when [A]aldehydes of the general formula (II)

in which $R^1$ has the meaning given above, are reacted with ketones of the general formula (III)

in which $R^2$ has the meaning given above, and enamines of the general formula (IV)

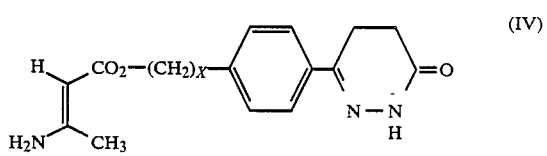

in which X has the meaning given above, in the presence of insert solvents, or when [LB]aldehydes of the general formula (II) are reacted with ketones of the general formula (V),

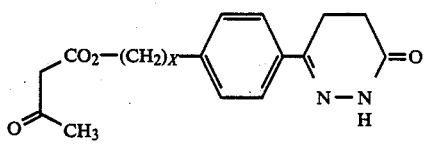

in which X has the meaning given above, and enamines of the general formula (VI)

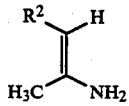

in which R² has the meaning given above, in the presence of inert solvents, or when [C]ketones of the general formula (III) are reacted with ammonia and ylidene compounds of the general formula (VII)

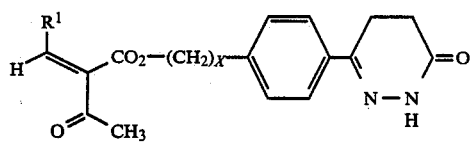

in which R¹ and X have the meaning given above, in the presence of inert solvents, or when [D]ketones of the general formula (V) are reacted with ammonia and ylidene compounds of the general formula (VIII)

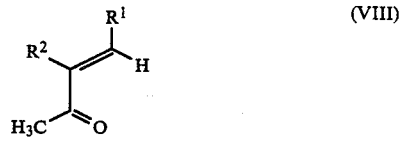

in which R¹ and R² have the meaning given above, in the presence of inert solvents, or when [E]enamines of the general formula (VI) are reacted with ylidene compounds of the general formula (VII) in the presence of inert solvents, or when [F]enamines of the general formula (IV) are reacted with ylidene compounds of the general formula (VII) in the presence of inert solvents.

According to the type of the starting compounds employed, the process variations A–F can be represented by the following scheme:

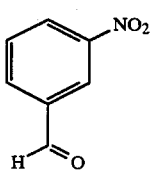

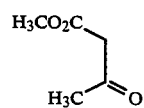

+

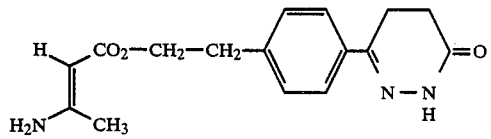

↓ [A]

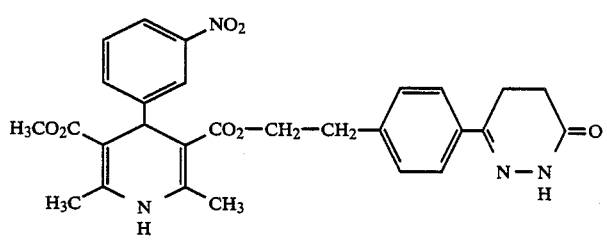

↑ [B]

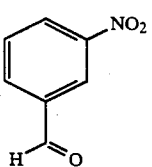

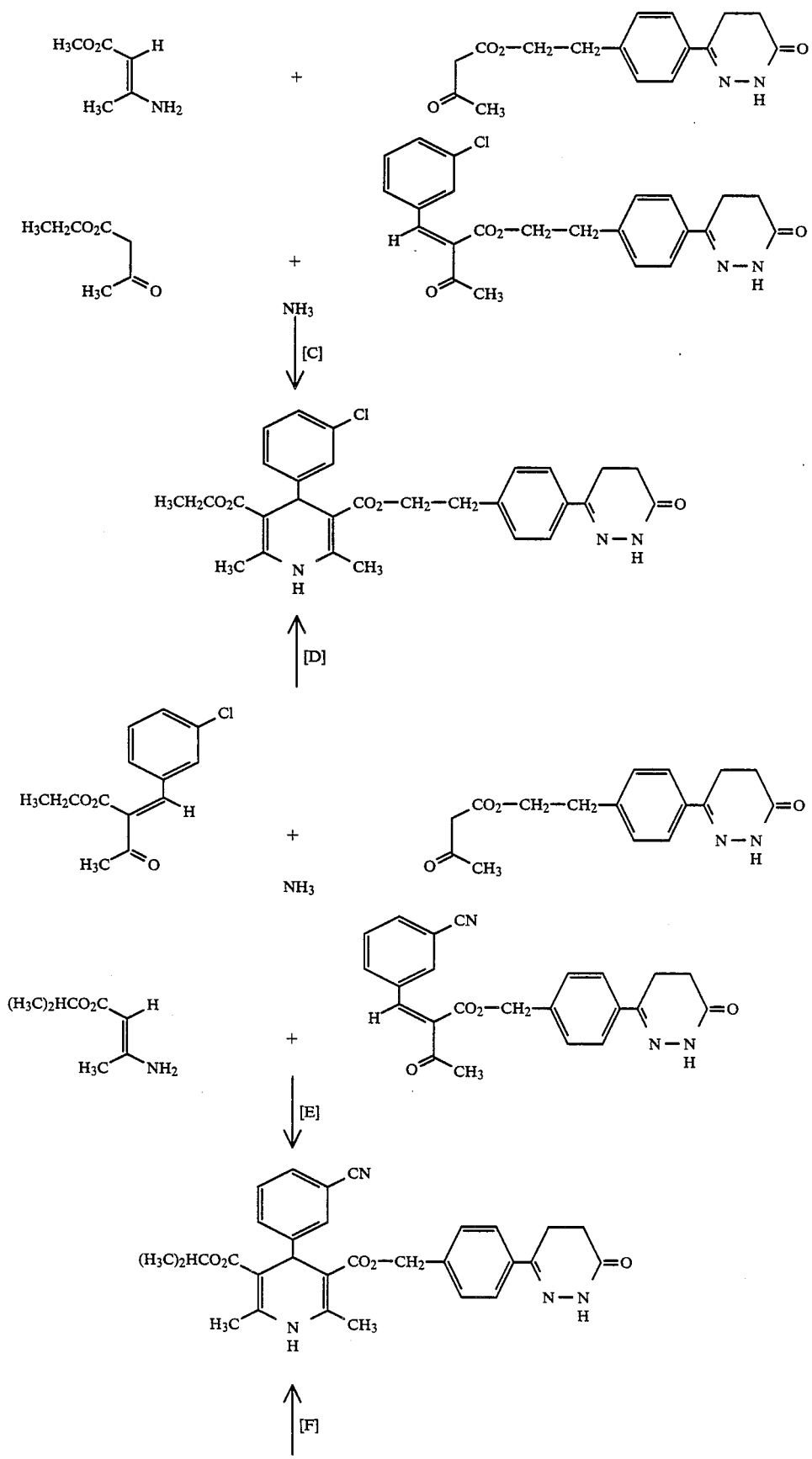

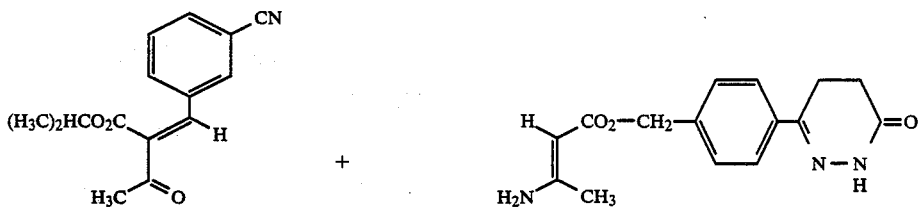

The aldehydes of the general formula (II) employed as starting substances are known or can be prepared by known methods [E. Mosettig, Organic Reactions III, 218, (1954); E.P. Papadopoulos, A. Jarrar, C.H. Isidorides, J. Org. Chem. 31, 615 (1966); A.J. Mancho, D.S. Brownfain, D. Swern, J. Org. Chem. 44, 4148 (1979)].

The ketones of the general formulae (III) and (IV) employed as starting substances are known or can be prepared by known methods [D. Borrmann, in Houben-Weyl's "Methoden der organischen Chemie" ("Methods of Organic Chemistry") VII/4, 230 (1968)].

The enamines of the general formulae (V) and (VI) employed as starting substances are known or can be prepared by known methods [S.A. Glickman, A.C. Cope, J. Am. Chem. Soc. 67, 1017 (1945)].

The ylidene compounds of the general formulae (VII) and (VIII) employed as starting substances are known or can be prepared by known methods [G. Jones, Organic Reactions, XV, 204 (1967)].

Water and all inert organic solvents which are not altered under the reaction conditions can be used as solvents for the processes A-F. Preferably included here are alcohols such as methanol, ethanol, propanol, isopropanol, ethers such as diethyl ether, dioxane or tetrahydrofuran, dimethylformamide, dimethyl sulphoxide, acetonitrile, acetic acid, ethyl acetate, hexamethylphosphoric triamide, or hydrocarbons such as benzene, toluene or xylene. Mixtures of the solvents mentioned can likewise be employed.

The reaction temperatures can be varied over a relatively large range for all the processes. In general, temperatures in a range of +10° C. to +200° C., preferably of +20° C. to 150° C., are used, in particular the boiling temperature of the solvent employed.

The reaction can be performed at atmospheric pressure, but also at increased or decreased pressure. In general atmospheric pressure is used.

In carrying out the process according to the invention the proportion of the substances required for the reaction is optional. In general, molar amounts of reactants are used. In processes C and D it has been shown to be advantageous to employ ammonia in up to a 20-fold, preferably up to a 10-fold, excess.

The compounds according to the invention exhibit a valuable spectrum of pharmacological activity which could not have been predicted. The substances of the formula (I) according to the invention act as inhibitors/stimulators of enzymatic reactions in the area of arachidonic acid metabolism. Such substances are suitable for the prophylaxis and treatment of diseases of the airways such as emphysema, shock lung, pulmonary hypertension, oedema, thrombosis and thromboembolism, ischaemia (peripheral, coronary, cerebral circulatory disturbances), coronary and cerebral infarctions, arrhythmias, angina pectoris, hypertension and also arteriosclerosis. The substances according to the invention are preferably inhibitors of thromboxane synthesis, and at the same time stimulate prostacyclin synthesis and have thrombocyte aggregationinhibiting activity.

The activities of the compounds according to the invention were detected by the following experiments:

I. $^3$H-Arachidonic acid metabolism

Arachidonic acid metabolism in human thrombocytes was investigated using tritium-labelled arachidonic acid. Thrombocytes metabolize arachidonic acid to $TXA_2$ and HHT via the cyclooxygenase pathway and to 12-HETE via the lipoxygenase pathway, which can be separated by thin layer chromatography [cf Bailey, J.M. et al., Prostaglandins 13, 479–492, (1977)], Inhibitors of the individual enzymatic reactions alter the chromatographic distribution pattern in a characteristic manner.

Washed human thrombocytes from healthy donors who had taken no drug for 14 days were incubated for 2 minutes at 37° C. with the test substance and then incubated for a further 10 minutes at 37° C. with $^3$H-arachidonic acid. The suspension was acidified and extracted with ethyl acetate. The ethyl acetate was evaporated off under a nitrogen atmosphere and the residue was taken up in methanol/trichloromethane (1:1) and applied to TLC plastic sheets. Separation was performed using a trichloromethane/methanol/glacial acetic acid/water (80:8:1:0.8) mobile solvent mixture. The distribution of radioactivity was measured by means of a radioscanner (Table 1).

II. Prostacyclin stimulation

The 1,4-dihydrophyridines to be used according to the invention additionally stimulate the synthesis of $PGI_2$. $PGI_2$ has vasodilating and thrombocyte aggregation inhibiting activity, in contrast with the vasoconstrictor and thrombocyte aggregation inhibitory action of thromboxan.

Stimulation in whole blood

In whole blood, collagen induces the formation of $PGI_2$. The endoperoxides formed in the thrombocytes are probably converted into $PGI_2$ by leucocytes. The stable end product of $PGI_2$ conversion, 6-keto-$PGF_1\alpha$, is determined radioimmunologically (Table 2).

III. Thrombocyte aggregation

Thrombocytes and their adhesion and aggregation capabilities are an essential pathogenetic factor in the formation of thromboses, particularly in the arterial branch of the circulatory system.

For the determination of thrombocyte aggregation inhibitory activity, blood from healthy subjects of both sexes was used. 9 parts of blood were mixed with one part of 3,8% aqueous sodium citrate solution as an anticoagulant. Platelet-rich citrate plasma (PRP) is obtained from this blood by means of centrifugation (Jürgen/Beller, Klinische Methoden der Blutgerinnungsanalyse (Clinical Methods of Blood Coagulation Analysis; Thieme Verlag, Stuttgart, 1959).

For these studies, 0.8 ml of PRP and 0.1 ml of the active substance solution were pre-incubated at 37° C. in a waterbath. Thrombocyte aggregation was then determined at 37° C. in an aggregometer (Therapeutische Berichte 47, 80–86, 1975) using the turbidometric method (Born, G.V.R., J. Physiol. (London), 162, 67, 1962). Aggregation was induced by adding 0.1 ml of collagen, an aggregation stimulating agent. The alteration of the optical density in the PRP sample was recorded during a 4 minute period and the alteration after 4 minutes was determined. From this the percentage inhibition compared to the control was calculated.

The range of the minimal effective concentrations is given as the minimal effective concentration (Table 3).

| Inhibition of $TXA_2$ synthesis | |
| --- | --- |
| Example No. | Minimal effective concentration for inhibition (MEC) [$\mu$g/ml] |
| 11 | 0.1 |
| 16 | 0.1 |
| 18 | 0.1 |
| 19 | 0.1 |
| 21 | 1–0.3 |
| 22 | <0.1 |

| Prostacyclin stimulation | |
| --- | --- |
| Example No. | Stimulation of $PGI_2$ synthesis (MEC) [$\mu$g/ml] |
| 11 | 1–0.1 |
| 21 | <3 |
| 22 | <1 |

| Inhibition of thrombocyte aggregation | |
| --- | --- |
| Example No. | Minimal effective concentration for inhibition (MEC) [$\mu$/ml] |
| 11 | 1–0.3 |
| 12 | 1–0.3 |
| 24 | 1–0.3 |
| 15 | 3–1 |
| 16 | 1–0.3 |
| 17 | 1–0.3 |
| 18 | 1–0.3 |
| 19 | 1–0.3 |
| 20 | 1–0.3 |
| 10 | <10 |
| 21 | <10 |
| 22 | 10–3 |
| 7 | 3–1 |
| 23 | 10–3 |
| 24 | 3–1 |
| 9 | 3–1 |

Moreover, the compounds according to the invention influence the contractility of the heart and the smooth muscle tone. They can therefore be employed in medicaments for influencing pathologically altered blood pressure, as coronary therapeutic agents and in the treatment of coronary insufficiency. Moreover, they can be used for the treatment of arrhythmias, for lowering blood sugar, for detumescence of the mucous membranes and for influencing the salt and liquid balance.

The coronary and circulatory activities were discovered using isolated perfused guineapig hearts.

For this, the hearts of 250 to 350 g guineapigs are used. The animals are killed by a blow to the head, the thorax is opened, and a metal cannula is tied into the exposed aorta. The heart is removed from the thorax with the lungs and is connected to the perfusion apparatus through an aortic cannula, with continuous perfusion. The lungs are removed at the lung roots. A Krebs Henseleit solution (1) (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$, 0.013 mmol/l of $Na_2EDTA$), which contains 1.2 mmol/l of $CaCl_2$, is used as the perfusion medium. 10 mmol/l of glucose are added as an energy-liberating substrate. Before the perfusion the solution is filtered until free of particles. The solution is gassed with Carbogen (95% $O_2$, 5% $CO_2$) in order to maintain a pH value of 7.4. The hearts are perfused at a constant flow rate (10 ml/min) at 32° C. using a peristaltic pump.

In order to measure the cardiac function, a latex balloon filled with liquid and connected through a column of liquid to a pressure gauge is introduced into the left ventricle through the left auricle, and the isovolumetric contractions are recorded on a high-speed recorder (Opie, L., J. Physiol. 180 (1965) 529–541). The perfusion pressure is recorded using a pressure gauge which is connected to the perfusion system upstream of the heart. Under these conditions a decrease in the perfusion pressure indicates coronary dilation, and a rise or fall in the amplitude of contraction of the left ventricle indicates an increase or decrease in cardiac contractility. The compounds according to the invention are infused into the perfusion medium at suitable dilutions just upstream of the isolated heart.

The following values show, as an example, the effect of the compounds according to the invention on isolated perfused guineapig hearts, expressed as the percentage difference to the starting pressure, set as equivalent to 100%.

| Example No. | Concentration (g/ml) | % alteration in contractility | % alteration in perfusion pressure |
| --- | --- | --- | --- |
| 7 | $10^{-6}$ | −60 | 0 |
| 11 | $10^{-6}$ | −23 | −36 |
| 13 | $10^{-6}$ | −78 | 0 |

The new active compounds can be converted in a known manner into the customary formulations, such as tablets, dragees, pills, granules, aerosols, syrups, emulsions, suspensions and solutions, using inert nontoxic, pharmaceutically suitable excipients or solvents. The therapeuically active compound should in each case be present in a concentration of about 0.5 to 90% by weight of the total mixture, that is to say in amounts which suffice to achieve the dosage range indicated.

The formulations are prepared, for example by extending the active compounds with solvents and/or excipients, optionally with the use of emulsifiers andor dispersing agents, and, for example when using water as a diluent, organic solvents can optionally be used as auxiliary solvents.

Examples of auxiliary substances which may be mentioned are: water, non-toxic organic solvents, such as paraffins (for example mineral oil fractions), vegetable oils (for exaqmple groundnut oil/sesame oil), alcohols (for example ethyl alcohol and glycerol), excipients, such as, for example, natural rock powders (for example kaolins, aluminas, talc and chalk), synthetic rock powders (for example highly disperse silica and silicates) and sugars (for example sucrose, lactose and glucose), emulsifiers (for example polyethylene fatty acid esters, polyoxyethylene fatty alcohol ethers, alkylsulphonates, and arylsulphonatrs), dispersing agents (for example lignin, sulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally, in particularly perlingually or intravenously. In the case of oral use, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium laurysulphate and talc, can be co-used when making tablets. In the case of aqueous suspensions, the active compounds can be mixed with various flavour-improving agents or colorants in addition to the abovementioned auxiliary substances.

In the case of parenteral use, solutions of the active compounds, employing suitable liquid excipients, can be used.

In general, it has proved advantageous, in the case of intravenous administration, to administer amounts of about 0.001 to 1 mg/kg, preferably about 0.01 to 0.5 mg/kg, of body weight to achieve effective results, and in the case of oral administration, the dosage is about 0.01 to 20 mg/kg, preferably 0.1 mg to 10 mg/kg, of body weight.

Nevertheless, it can at times be necessary to deviate from the amounts mentioned, and in particular to do so as a function of the body weight or of the nature of the administration method, the animal's individual behavior towards the medicament, the nature of the formulation of the medicament and the time or interval at which the administration takes place. Thus it can suffice in some cases to manage with less than the above-mentioned minimum amount, while in other cases the upper limit mentioned must be exceeded. Where relatively large amounts are administered, it can be advisable to divide these into several individual administrations over the course of the day.

PREPARATION EXAMPLES

EXAMPLE 1

4-Oxo-4-[4-(tetrahydropyran-2-yl-oxymethyl)-phenyl]butyric acid

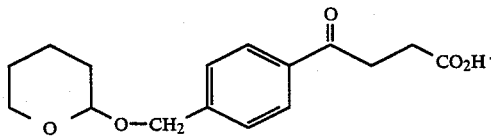

Under an inert gas, 12.75 g (0.53 mol) of magnesium turnings in 200 ml of tetrahydrofuran are activated with a little iodine, and then 135 g of p-bromobenzyliodine tetrahydropyranyl ether are slowly added dropwise. The reation is strongly exothermic. In order to complete the reaction, the mixture is stirred for a further 2 hours with warming. The solution is cooled to −80° C., and 53 g of succinic anhydride, suspended in 200 ml of tetrahydrofuran are added in portions. The mixture is then stirred for a further 2 hours and hydrolyzed using 4 l of water, and the pH is adjusted to 8 using 2 N sodiumhydroxide solution. Washing is carried out using methylene chloride. The aqueous phase is adjusted to pH 4.5 using citric acid. The product is extracted with methylene chloride, the extracts are dried and the product is precipitated by addition of petroleum ether.

Melting point: 97° C..

Yield: 59 g (40.4% of theory).

EXAMPLE 2

[4-(6-Oxo-1,4,6-tetrahydropyridazin-3-yl)benzyl]-tetrahydropyran-2-yl ether

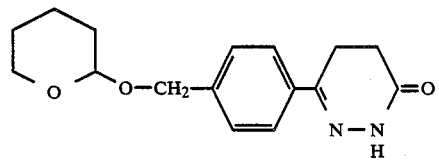

50 g of 4-oxo-4-[4-(tetrahydropyran-2-yl-oxymethyl)-phenyl]-butyric acid (Example 1) are suspended in 240 ml of water and the suspension is stirred for 3 hours at 90° C. with 10 ml of hydrazine hydrate. After cooling, the precipitated crystals are filtered off with suction. The aqueous phase is extracted with methylene chloride, and this extract is dried and evporated. The residue is triturated with ether. Yield: 42 g (84% of theory)

EXAMPLE 3

4-(6-Oxo-1,4,5,6-tetrahydropyridazin-3-yl)benzyl alcohol

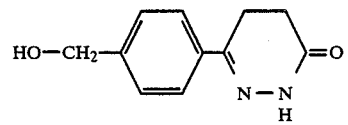

48 g of [4-(6-oxo-1,4,5,6-tetrahydropyridazin-3-yl)benzyl]-tetrahydropyran-2-yl ether (Example 2) are dissolved in 600 ml of tetrahydrofuran and the solution is treated with 100 ml each of glacial acetic acid, 1 N hydrochloric acid and water. After standing for 24 hours at room temperature, the tetrahydrofuran is distilled off and the residue is extracted with methylene chloride. The product is partly precipitated as a result and is filtered off with suction. The methylene chloride phase is worked up. The two batches of crystals are combined.

Melting point: 188° C.

Yield: 26.3 g (74% of theory).

EXAMPLE 4

4-(6-Oxo-1,4,5,6-tetrahydropyridazin-3-yl)benzyl acetoacetate

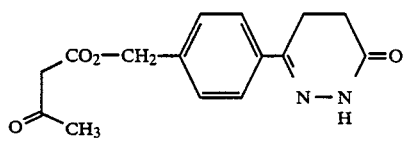

20 g of 4-(6-oxo-1,4,5,6-tetrahydropyridazin-3-yl)benzyl alcohol (Example 3) are suspended in 50 ml of tetrahydrofuran and, after addition of 100 mg of 4-dimethylamino-pyridine, the suspension is reacted under reflux with 10.7 g of diketene. The mixture is reacted for a further 2 hours. The compound crystallizes after evaporation of part of the tetrahydrofuran and addition of ethanol.

Yield: 20.6 g (73% of theory).
Melting point: >200° C.

EXAMPLE 5

4-(6-Oxo-1,4,5,6-tetrahydropyridazin-3-yl)benzyl β-aminocrotonate

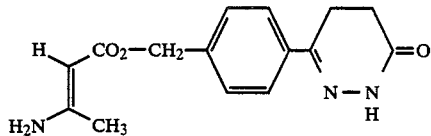

10 g of 4-(6-oxo-1,4,5,6-tetrahydropyridazin-3-yl)benzyl acetoacetate (Example 4) are suspended in 100 ml of dry tetrahydrofuran, and the suspension is saturated with ammonia gas at the reflux temperature. After allowing the mixture to cool overnight, the tetrahydrofuran is evaporated off and the residue is purified by boiling with isopropanol.

Yield: 9.5 g (94% of theory).
Melting point: 183° C.

EXAMPLE 6

2-[4-6-Oxo-1,4,5,6-tetrahydropyridazin-3-yl)phenyl]ethyl β-aminocrotonate

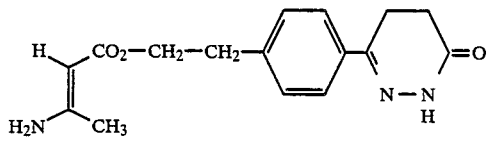

From 4-(6-oxo-1,4,5,6-tetrahydropyridazin-3-yl)phenylethyl alcohol obtained analogously to Example 3 and diketene, the acetoacetate is obtained analogously to Example, 4 and converted into the desired β-aminocrotonate using ammonia as in Example 5.

Yield: 64% of theory.

EXAMPLE 7

Ethyl 4-(6-oxo-1,4,5,6-tetrahydropyridazin-3-yl)benzyl 1,4-dihydro-2,6-dimethyl-4-(3-nitrophenyl)-pyridine-3,5-dicarboxylate

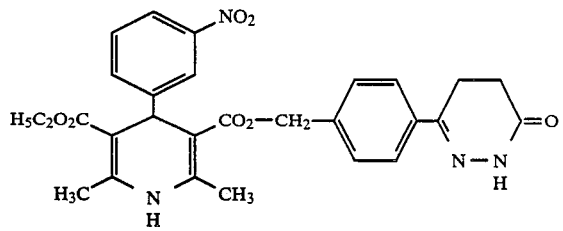

10.0 mmol of 3;-nitrobenzaldehyde, 10 mmol of ethyl acetoacetate and 10 mmol of 4-(6-oxo-1,4,5,6-tetrahydro-pyridazin-3-yl)benzyl β-aminocrotonate are heated under reflux for 12 hours in isopropanol. The product crystallizes on cooling.

Melting point: 258° C.
Yield: 62% of theory

EXAMPLE 8

4-(6-Oxo-1,4,5,6-tetrahydropyridazin-3-yl)benzyl 2-chlorobenzylidene acetoacetate

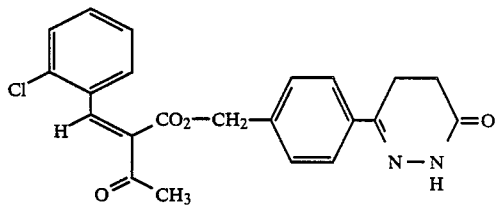

20 mmol of 2-(n-butyliminomethyl)-chlorobenzene and 20 mmol of 4-(6-oxo-1,4,5,6-tetrahydropyridazin-3-yl) benzyl acetoacetate are added at the same time to 30 ml of acetic anhydride and, after heating for a short while, the mixture is stirred for 24 hours at room temperature. The batch is then added to 250 ml of ice-water, the mixture is stirred for 2 hours, and the precipitate is filtered off and purified by boiling with a little ethanol.

Melting point: 192° C.
Yield: 63% of theory.

EXAMPLE 9

Isopropyl 4-(6-oxo-1,4,5,6-tetrahydropiperazin-3-yl)benzyl 4-(2-chlorophenyl)-1,4,-dihydro-2,6-dimethylpyridine-3,5-dicarboxylate

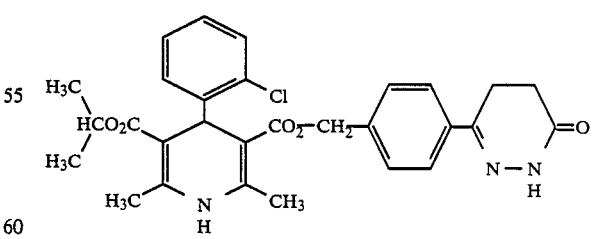

10 mmol of isopropyl β-aminocrotonate and 4-(6-oxo-1,4,5,6-tetrahydropyridazin-3-yl)benzyl 2-chlorobenzylidene acetoacetate are heated to reflux for 8 hours in 30 ml of isopropanol. The product crystallizes on trituration after cooling.

Melting point: 211° C.
Yield: 73% of theory

EXAMPLE 10

Mono-2-[4-(6-oxo-1,4,5,6-tetrahydropyridazin-3-yl)phenyl]ethyl 1,4-dihydro-2,6-dimethyl-4-(2-pyrid-2-yl-ethyl)pyridine-3,5-dicarboxylate

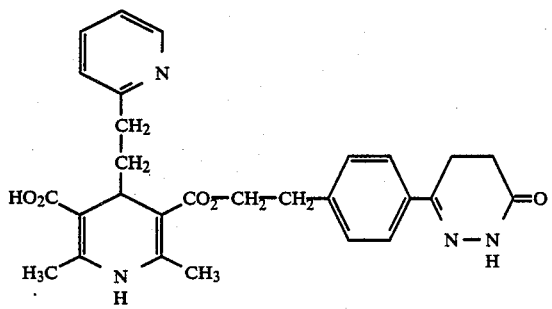

5 mmol of 2-cyanoethyl 2-[4-(6-oxo-1,4,4,6-tetrahydropyridazin-3-yl)phenyl]ethyl 1,4-dihydro-2,6-dimethyl-4-(2-pyrid-2-yl-ethyl)-pyridine-3,5-dicarboxylate are dissolved in 20 ml of dimethoxyethane. 15 mmol of sodium hydroxide in 30 ml of water are added to the solution, which is stirred for 6 hours at room temperature. The dimethoxyethane is then distilled off from the solution in vacuo, the aqueous residue is extracted with methylene chloride, the extracts are then acidified to pH 2, and the precipitated product is stirred with 10 ml of ethanol after filtering off with suction.

Melting point: 218° C.
Yield: 82% of theory

The examples according to the invention which are listed in the table below were obtained analogously to the described examples.

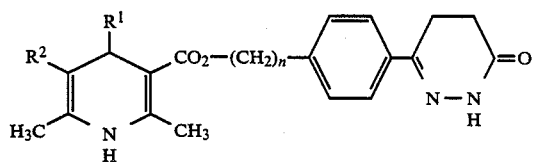

| No. | $R^1$ | $R^2$ | n | Melting point [°C.] |
|---|---|---|---|---|
| 11 | —(CH₂)₂—(3-pyridyl) | (3-pyridyl)—(CH₂)₃—O₂C— | 1 | Foam |
| 12 | (3-pyridyl)— | (3-pyridyl)—(CH₂)₃—O₂C— | 1 | 208 Decomp. |
| 13 | 2-Cl-phenyl | $H_3CO_2C-$ | 1 | 259 |
| 14 | 2,3-diCl-phenyl | $H_5C_2O_2C-$ | 1 | 264 |
| 15 | 2-OCH₃-phenyl | $H_5C_2O_2C-$ | 1 | 240 |
| 16 | —(CH₂)₂—(3-pyridyl) | $H_3CO_2C-$ | 1 | 220 |
| 17 | —(CH₂)₂—(3-pyridyl) | NC—CH₂—CH₂—O₂C— | 1 | 182 |

-continued

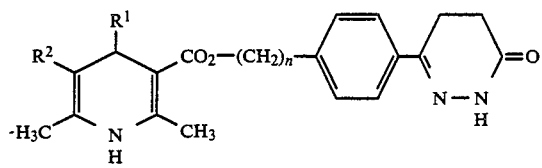

| No. | R¹ | R² | n | Melting point [°C.] |
|---|---|---|---|---|
| 18 | −(CH₂)₂−(3-pyridyl) | H₃C−CO− | 1 | 220 |
| 19 | −(CH₂)₂−(3-pyridyl) | NC− | 1 | 175 |
| 20 | −(CH₂)₂−(3-pyridyl) | H₂N−CO− | 1 | 128 |
| 21 | −(CH₂)₂−(3-pyridyl) | H₃CO₂C− | 2 | 148 |
| 22 | −(CH₂)₂−(3-pyridyl) | (3-pyridyl)−(CH₂)₃O₂C− | 2 | 159 |
| 23 | 2-methyl-thiochromone-3-phenyl | 4-[(3-oxo)pyridazinyl]phenyl−H₂CO₂C− | 1 | 187 |
| 24 | 3-ethoxyphenyl | C₆H₅CH₂−N(CH₃)−(CH₂)₂−O₂C− | 2 | 193 |
| 25 | 2-(benzylthio)phenyl | pyrrolidinyl−N−(CH₂)₂−O₂C− | 1 | 216 |
| 26 | 7-methyl-benzofurazanyl | H₃CO−CH₂−CH₂−O₂C− | 1 | 227 |
| 27 | 2-(trifluoromethyl)phenyl | Br−(CH₂)₃−O₂C− | 2 | 163 |

It will be appreciated that the instant specification and claims are set forth by way of illustration and not limitation, and that various modifications and changes may be made without departing from the spirit and scope of the present invention.

What is claimed is:

1. A 1,4-dihydropyridine of the formula

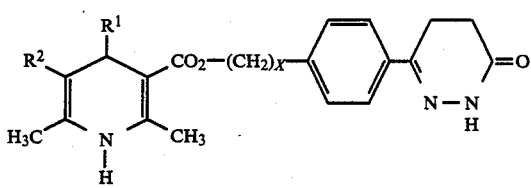

in which

R¹ represents phenyl or naphthyl, which may be mono- or independently di- or tri- substituted by fluorine, chlorine, bromine, nitro, cyano, $C_1$-$C_4$-alkyl, $C_1$-$C_4$-alkoxy, $C_1$-$C_4$-alkylthio, trifluoromethyl, trifluoromethoxy, difluoromethoxy, trifluoromethylthio, benzylthio or benzyloxy which is optionally substituted by nitro, fluorine, chlorine, bromine, trifluoromethyl, methyl or methoxy, or represents an optionally methyl-, fluorine-, chlorine-, bromine- or phenylsubstituted heterocycle from the series thienyl, furyl, pyridyl, pyrimidyl, quinolyl, benzoxadiazolyl or thiochromenyl, or represents straight-chain or branced, optionally fluorine-, chlorine- bromineor pyridyl- substituted alkyl with up to 4 carbon atoms, R² represents cyano or a group of the formula

wherein R³ represents straight-chain, branched or cyclic alkyl with up to 6 carbon atoms, or represents a group of the formula

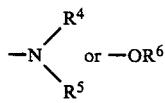

where

R⁴ and R⁵ are identical or different and represent hydrogen, $C_1$-$C_4$-alkyl or phenyl, and R⁶ represents hydrogen or represents straight-chain or branched alkyl with up to 8 carbon atoms, which can be substituted by up to 7 fluorine atoms, or by chlorine, bromine, cyano, hydroxyl, $C_1$-$C_6$-alkoxy, pyridyl, phenoxy or by phenyl which is optionally substituted by fluorine, chlorine, bromine, nitro, cyano, trifluoromethyl, $C_1$-$C_2$-alkyl, $C_1$-$C_2$-alkoxy or a group of the formula

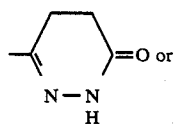

by a group of the formula

where

R⁷ and R⁸ are identical or different and represent hydrogen, $C_1$-$C_4$-alkyl, phenyl, benzyl or acetyl, or R⁷ and R⁸ together form a 5-or 7-membered ring, which optionally contains sulphur or oxygen as a further hetero atom, and X represents a number from 0 to 5, or a physiologically acceptable salt thereof.

2. A compound or salt according to claim 1, in which

R¹ represents phenyl, which may be mono- independently di-substituted by fluorine, chlorine, nitro, cyano, $C_1$-$C_4$-alkyl, $C_1$-$C_4$-alkoxy, trifluoromethyl, benzyloxy or benzylthio, or represents thienyl, furyl, pyridyl or benzoxadiazolyl or, represents a heterocycle of the formula

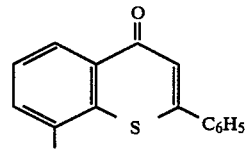

or represents an optionally α-, β- or γ-pyridylsubstituted methyl or ethyl,

R³ represents straight-chain or branched alkyl with up to 4 carbon atoms, or represents a radical of the formula

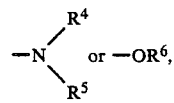

where

R⁴ and R⁵ are identical or different and represent hydrogen, methyl or ethyl and R⁶ represents hydrogen or represents a straight-chain or branched alkyl with up to 6 carbon atoms, which may be mono-, di- or tri-substituted by fluorine, chlorine, bromine, cyano, hydroxyl, $C_1$-$C_4$-alkoxy, α-, β-or γ-pyridyl or by a group of the formula

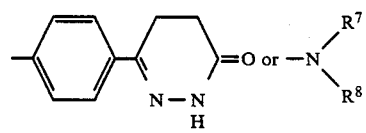

wherein

R⁷ and R⁸ are identical or different and represent hydrogen, methyl, ethyl or benzyl, or R⁷ and R⁸ together form a pyrrolidino or piperidine ring, and X represents a number from 1 to 4.

3. A compound according to claim 1, wherein such compound is

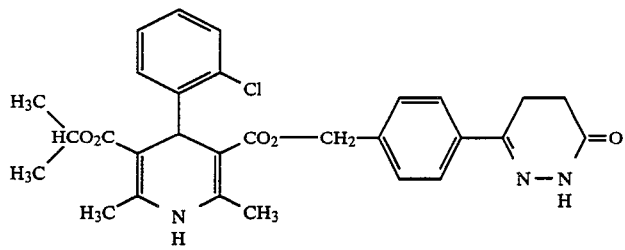

or a physiogically acceptable salt thereof.

4. A compound according to claim 1, wherein such compound is

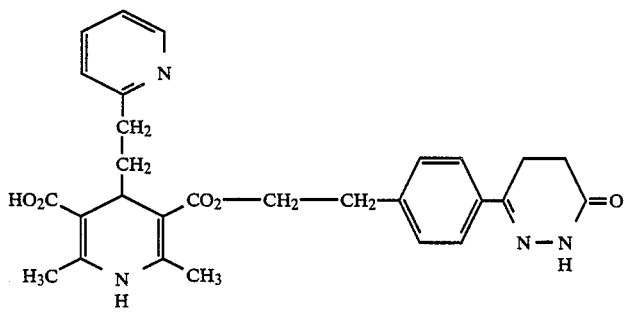

or a physiologically acceptable salt thereof.

5. A compound according to claim 1, wherein such compound is or a physiologically acceptable salt thereof.

6. A compound according to claim 1, wherein such compound is

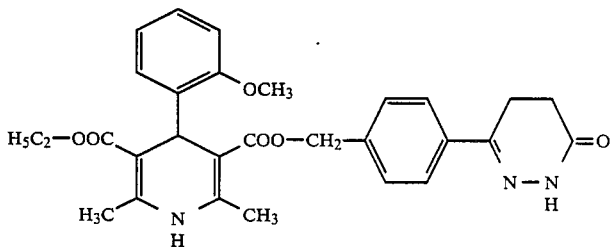

or a physiologically acceptable salt thereof.

7. A compound according to claim 1, wherein such compound is

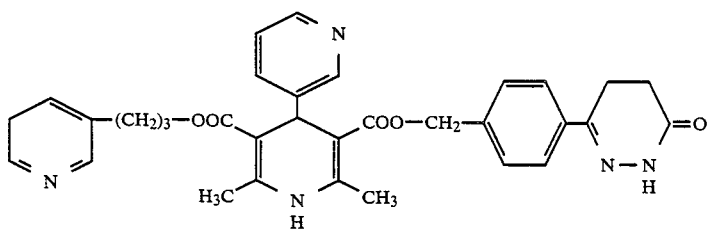

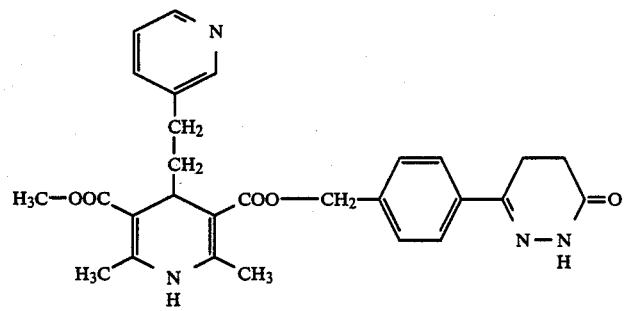

or a physiologically acceptable salt thereof.

8. A compound according to claim 1, wherein such compound is

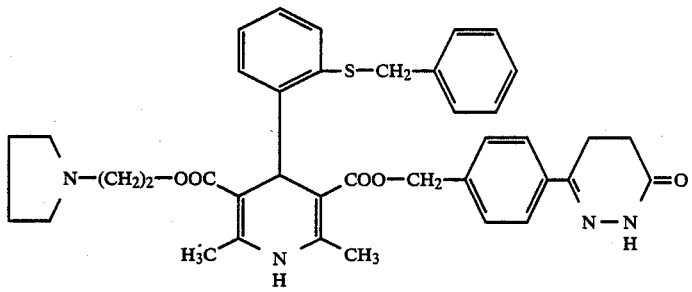

or a physiologically acceptable salt thereof.

9. A composition for the prophylaxis and treatment of a disease of the airway, ischaemia, coronoary or cerebral infarction, arrhythmia, angina pectoris, hypertension or arterioscherosis comprising an effective amount therefor of a compound or salt according to claim 1 and a diluent.

10. A unit dose of a composition according to claim 9 in the form of a tablet, ampoule or capsule.

11. A method of treating a patient for a disease of the airway, ischaemia, coronary or cerebral infarction, arrhythmia, angina pectoris, hypertension or arterioscherosis which comprises administering to such patient an amount effective therefor of a compound or salt according to claim 1.

12. The method according to claim 11, wherein such compound is

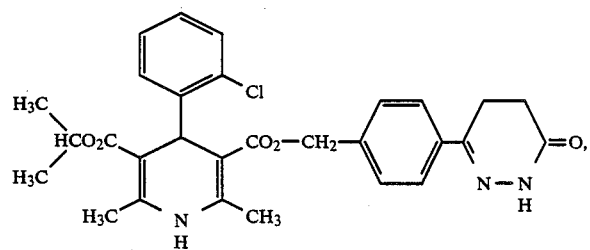

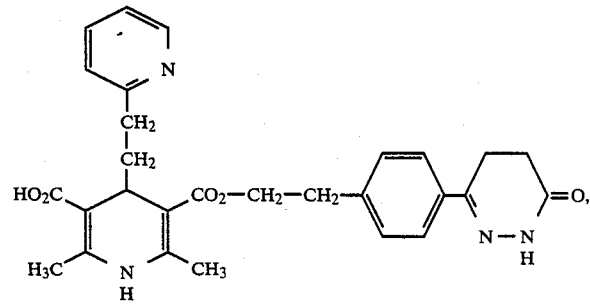

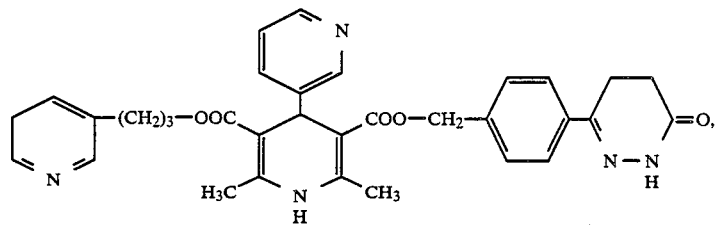
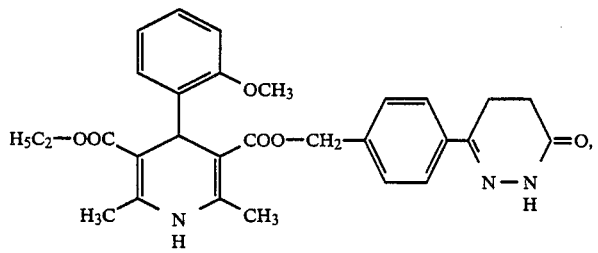
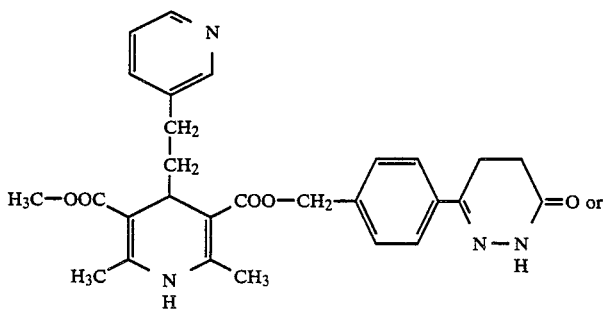
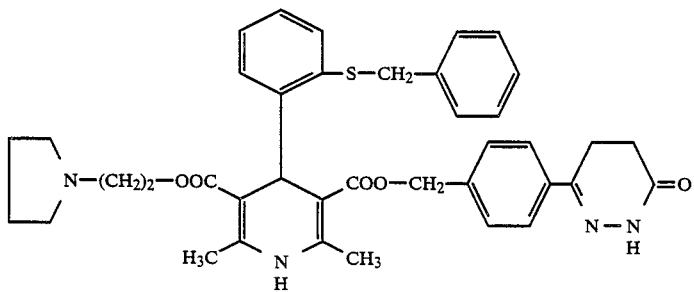
or a physiologically acceptable salt thereof.
* * * * *